US008668908B2

(12) United States Patent
Wu

(10) Patent No.: US 8,668,908 B2
(45) Date of Patent: Mar. 11, 2014

(54) **METHOD FOR ALLEVIATING CHEMOTHERAPY SIDE EFFECTS USING EXTRACT OF *DIOSCOREA* SP**

(75) Inventor: Rong-Tsun Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 1182 days.

(21) Appl. No.: 12/327,162

(22) Filed: Dec. 3, 2008

(65) Prior Publication Data
US 2009/0136600 A1 May 28, 2009

Related U.S. Application Data

(63) Continuation-in-part of application No. 11/274,775, filed on Nov. 15, 2005, which is a continuation-in-part of application No. 10/335,278, filed on Dec. 31, 2002, now abandoned.

(51) Int. Cl.
*A61K 36/8945* (2006.01)
*A61K 39/395* (2006.01)

(52) U.S. Cl.
USPC .......................... 424/130.1; 435/2; 514/885

(58) Field of Classification Search
None
See application file for complete search history.

(56) References Cited

U.S. PATENT DOCUMENTS

| | | | |
|---|---|---|---|
| 2,774,713 | A | 12/1956 | Gould et al. |
| 3,620,919 | A | 11/1971 | Hardman |
| 5,407,684 | A | 4/1995 | Loria et al. |
| 5,863,593 | A | 1/1999 | Juarez |
| 5,968,917 | A | 10/1999 | Clayton |
| 6,113,907 | A | 9/2000 | Khwaja et al. |
| 6,593,310 | B1 | 7/2003 | Cullis-Hill |
| 6,750,248 | B2 | 6/2004 | Yong et al. |
| 6,998,262 | B2 | 2/2006 | Wu |
| 7,645,463 | B2 | 1/2010 | Wu |
| 2002/0049182 | A1 * | 4/2002 | Von Borstel et al. ........... 514/44 |
| 2006/0068036 | A1 | 3/2006 | Wu |

FOREIGN PATENT DOCUMENTS

| | | | |
|---|---|---|---|
| CN | 1227261 A | * | 9/1999 |
| IN | 78983 | | 10/1961 |
| WO | WO 02/67961 | * | 3/2002 |

OTHER PUBLICATIONS 2011 http://www.cancer.gov/cancertopics/coping/chemo-side-effects.*

Abroshnikova et al., "Steroid saponins and diosgenin in a tissue culture of Disocorea deltoidea," Khimiko-Farmatsevticheskii Zhurnal 6(4):20-21 (1972).
Aradhana et al., "Diosgenin—a growth stimulator of mammary gland of ovariectomized mouse," Indian J. Exp. Biol., 30(5):367-70 (May 1992) (Abstract only).
Araghiniknam et al., "Antioxidant Activity of *Dioscorea* and Dehydroepiandrosterone (DHEA) in Older Humans," Life Sciences, 59(11):PL-147-157 (1996).
Arinze, "The Occurrence of Antifungal Compounds in Yam Tissues in Response to Penicilium scleretigenum," J. Mycology and Plant Pathology, 31, pp. 287-291 (2001).
Barrett-Connor et al., "Horomone replacement therapy (HRT)—risks and benefits," International Journal of Epidemiology, 30:423-426 (2001).
Bell et al., "High-fructose feeding of streptozotocin-diabetic rats is associated with increased cataract formation and increased oxidative stress in the kidney," British Journal of Nutrition 84, 575-582 (2000).
Beneytout et al., "A Plant Steroid, Diosgenin, A New Megakaryocytic Differentiation Inducer of Hel Cells," Biochemical and Biophysical Research Communications, 207(1):398-404 (Feb. 6, 1995).
Cruz et al., "Statins and osteoporoisis: Can these lipid-lowering drugs also bolster bones?," Cleveland Clinic Journal of Medicine, vol. 69, No. 4, pp. 277-288 (Apr. 2002).
*Dioscorea*, Wikipedia, the free encyclopedia, printout from http://en.wikipedia.org/wiki/dioscorea, print out date: Feb. 20, 2008, 5 pages.
Dixit et al., "Genetic stability assessment of plants regenerated from cryopreserved embryogenic tissues of *Dioscorea bulbifera* I. using RAPD, biochemical and morphological analysis," Cryo Letters, 24(2):77-84 (Mar.-Apr. 2003).
Herzberg et al., "Conflicting Results Obtained by RAPD-CR and large subunit rDNA Sequences in Determining and Comparing Yeast Strains Isolated from Flowers: A Comparison of Two Methods," International Journal of Systemic and Evolutionary Microbiology, 52, 1423-1433 (2002).
Kaufman et al., "Molecular and Cellular Methods in Biology and Medicine," CRC Press, Inc. p. 439 (1995).
Liu et al., "Estrogen Inhibition of PTH-Stimulated Osteoclast Formation and Attachment in Vitro: Involvement of Both PKA and PKC," Endocrinology 143(2):627-635 (2002).
Lorenzetti et al., "Effects of Phytoestrogens on Osteoclast Differentiation: A Murine Model of Rankl-Induced Osteoclastogenesis to Study the Biological Effects of Plant-Derived Compounds," Proceedings fo the XLVIII Italian Society of Agricultural Genetics—SIFV-SIGA Joint Meeting, 2 pages (Sep. 2004).

(Continued)

*Primary Examiner* — Patricia Leith
*Assistant Examiner* — Catheryne Chen
(74) *Attorney, Agent, or Firm* — Volpe and Koenig, P.C.

(57) ABSTRACT

Extract fractions of *Dioscorea* sp. and methods of preparing the extract fractions are disclosed. The extract fractions enhance the proliferation and differentiation of bone marrow cells. Also described are a method for treatment of osteoporosis and a method for alleviation of side effects caused by chemotherapy by using the extract fractions of *Dioscorea* sp.

4 Claims, 10 Drawing Sheets

(56) References Cited

OTHER PUBLICATIONS

Medline Plus, "Wild Yam (*Dioscorea villosa*)," printout from website: http://www.nlm.nih.gov/medlineplus/druginfo/natural/patient-wildyam.html, 4 pages (Feb. 1, 2008).

National Cancer Institute, "Chemotherapy Side Effects Fact Sheets," http://www.cancer.gov/cancertopics/coping/chemo-side-effects.

Rasper et al., "Anthocyanins of *Dioscorea alata* L.," Cellular and Molecular Life Sciences, 23: 611-612 (1967).

Scheven et al., "Dehydroepiandrosterone (DHEA) and DHEA-S Interact with 1,25-Digydroxyvitamin D3 (1,25(OH)2D3) to Stimulate Human Osteoblastic Cell Differentiation," Life Sciences, 62(1):59-68 (1998).

Wei et al., "Isoflavone Genistein: Photoprotection and Clinical Implications in Dermatology," International Research Conference on Food, Nutrition, and Cancer, J. Nutr. 133:3811S-3819S (2003).

Yamaguchi et al., "Pharmacological Effects of Three Products of Chinese Herbal Remedies on Experimental Osteoporosis Induced by Ovariectomy in Rats," Oyo Yakuri Pharmacometrics, 57(1/2) 13-30 (1999) (in Japanese with English language abstract and English language tables).

Non-Final Rejection, U.S. Appl. No. 11/274,775, dated Jan. 3, 2008.
Final Rejection, U.S. Appl. No. 11/274,775, dated Oct. 23, 2008.
Non-Final Rejection, U.S. Appl. No. 11/274,775, dated May 22, 2009.
Final Rejection, U.S. Appl. No. 11/274,775, dated Feb. 25, 2010.
Non-Final Rejection, U.S. Appl. No. 11/274,775, dated Sep. 24, 2010.
Final Rejection, U.S. Appl. No. 11/274,775, dated Mar. 17, 2011.
Non-Final Rejection, U.S. Appl. No. 12/324,076, dated Jun. 23, 2011.
Final Rejection, U.S. Appl. No. 10/335,278, dated Jul. 15, 2005.
Non-Final Rejection, U.S. Appl. No. 10/335,278, dated Jun. 30, 2004.
Requirement for Restriction/Election, U.S. Appl. No. 10/335,278, dated Apr. 15, 2004.

* cited by examiner

Actin     0     40     200     1000   (mg/ml)

BMP-2    0     40     200     1000   (mg/ml)

TGF-β    0     40     200     1000   (mg/ml)

IL-4      0     40     200     1000   (mg/ml)

Control:
N2 medium with 10 ng/ml EGF

DioMs 0.1 µg/ml

Positive ctrl:
N2 medium with EGF 50 ng/ml

DioMs 1 µg/ml

DioMs 10 µg/ml

SEQUENCE LISTING

<160> NUMBER OF SEQ ID NOS: 8

<210> SEQ ID NO 1
<211> LENGTH: 23
<212> TYPE: DNA
<213> ORGANISM: Artificial
<220> FEATURE:

-continued

<223> OTHER INFORMATION: primer

<400> SEQUENCE: 1
atgggtctca accccagct agt                                                  23

<210> SEQ ID NO 2
<211> LENGTH: 24
<212> TYPE: DNA
<213> ORGANISM: Artificial
<220> FEATURE:
<223> OTHER INFORMATION: primer

<400> SEQUENCE: 2
gctctttagg ctttccagga agtc                                                24

<210> SEQ ID NO 3
<211> LENGTH: 41
<212> TYPE: DNA
<213> ORGANISM: Artificial
<220> FEATURE:
<223> OTHER INFORMATION: primer

<400> SEQUENCE: 3
tggaccgcaa caacgccatc tatgccatct atgagaaaac c                             41

<210> SEQ ID NO 4
<211> LENGTH: 32
<212> TYPE: DNA
<213> ORGANISM: Artificial
<220> FEATURE:
<223> OTHER INFORMATION: primer

<400> SEQUENCE: 4
tggagctgaa gcaatagttg gtatccaggg ct                                       32

<210> SEQ ID NO 5
<211> LENGTH: 17
<212> TYPE: DNA
<213> ORGANISM: Artificial
<220> FEATURE:
<223> OTHER INFORMATION: primer

<400> SEQUENCE: 5
catccagccg acccttg                                                        17

<210> SEQ ID NO 6
<211> LENGTH: 18
<212> TYPE: DNA
<213> ORGANISM: Artificial
<220> FEATURE:
<223> OTHER INFORMATION: primer

<400> SEQUENCE: 6
ctctcccact gacttgtg                                                       18

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
gactacctca tgaagatcct                                                     20

<210> SEQ ID NO 8

-continued

```
<211> LENGTH: 20
<212> TYPE: DNA
<213> ORGANISM: Artificial
<220> FEATURE:
<223> OTHER INFORMATION: primer

<400> SEQUENCE: 8
ccacatctgc tggaaggtgg                                               20
```

METHOD FOR ALLEVIATING CHEMOTHERAPY SIDE EFFECTS USING EXTRACT OF *DIOSCOREA* SP

CROSS-REFERENCE TO RELATED APPLICATIONS

The present application is a continuation-in-part of application Ser. No. 11/274,775, filed on Nov. 15, 2005, which is a continuation-in-part of application Ser. No. 10/335,278, filed on Dec. 31, 2002, now abandoned. Each of the prior applications is hereby incorporated herein by reference in its entirety. The present application discloses and claims the non-elected subject matter from application Ser. No. 10/335,278.

BACKGROUND OF THE INVENTION

The present invention relates to an oral composition comprising an active extract of certain species of the genus *Dioscorea*, in particular to an oral composition capable of enhancing the proliferation and differentiation of cells, and of alleviating the side effects induced by chemotherapy. The present invention provides a method for treatment of osteoporosis and a method for alleviation of side effects caused by chemotherapy.

Plants of the genus *Dioscorea*, also known as "wild yam," are members of the monocotyledonous family Dioscoreaceae, which is distributed in the tropical and subtropical regions. There are about 650 species in the world, of which 93 species and 9 varieties are found in China, and 14 species and 5 varieties are found in Taiwan.

*Dioscorea* is one of the very important pharmaceutical plants used in traditional Chinese medicine, and the medicinal effects thereof have been studied for years. In 1936, Tsukamoto et al isolated diosgenin, a steroid saponin of *Dioscorea*, from Dioscoreacea family of plants and then use it as raw material for rapid synthesis of medicinal steroids. In Aradhana, M., Rao, A. C. and Kale, R. K., *Indian Journal of Experimental Biology* 30:367-370, 1992, it was indicated that diosgenin promotes the growth of epithelial cells of rat mammary glands. Beneytout, J. L., et al., *Biochemical & Biophysical Research Communications* 207(1):398-404, February 1995, reported that diosgenin induces morphological and biochemical changes characteristic of megakaryocyte cells when diosgenin is added to human erythroleukemia (HEL) cell cultures and, thus, diosgenin can be used as a megakaryotic differentiation inducer of HEL cells. In Araghiniknam, M., et al., *Life Sciences* 59(11):147-157, 1996, a steroid extract of *Dioscorea* was indicated to possess significant activities as an anti-oxidant to modify serum lipid levels.

Dehydroepiandrosterone (DHEA) has a similar chemical structure to diosgenin, and is known to have anti-cancer, anti-oxidation, and anti-diabetic effects, as well as an effect on the regulation of bone mass. The serum levels of DHEA gradually decrease as age increases, and are related to aging. It was speculated from various studies that the diosgenin extract of *Dioscorea* might be converted into DHEA in the human body and thus supplements the DHEA which decreases with aging. However, these studies were only conducted on old people taking diosgenin present in the *Dioscorea* to investigate if diosgenin could reduce the over-oxidation of serum lipids, lower the triglycerides in blood serum and increase high density level (HDL) of cholesterol while decreasing the over-oxidation damage of low density level (LDL) of cholesterol.

Concerning the effect of DHEA on regulation of bone mass, Scheven, B. A. A., et al., *Life Science* 62(1):59-68, 1998, reported that DHEA and its sulfate derivative (DHEA-S) failed on their own to exert direct, independent, significant effects on the growth and differentiation of human osteoblastic cells, but treating the cells in conjunction with a bone cell modulating agent, 1,25-dihydroxyvitamin $D_3$, (1,25(OH)$_2$D$_3$), resulted in enhancement of specific alkaline phosphatase (ALP) activity, which is the specific marker of maturing osteoblastic cells. This study shows that the effects of DHEA and DHEA-S on osteoblastic cell growth and differentiation are likely to be mediated via an effect on 1,25 (OH)$_2$D$_3$-induced change in bone cells.

In accordance with the present invention, it was found that the extract of a particular *Dioscorea* species harvested from the Yang-Ming Mountain in Taiwan, R.O.C., *Dioscorea alata* L. cv. Phyto, which has been given the scientific name "*Dioscorea alata* (No. YMM-PH3)" by the Research Center for Drug Discovery at the National Yang Ming University, Taipei, Taiwan, R.O.C., (referred to hereinafter as "*Dioscorea alata* L. cv. Phyto"), and further extracted fractions possess biological activity on cell regeneration.

Specifically, it was found that the extract of the *Dioscorea alata* L. cv. Phyto and the further extracted fractions per se, and it is believed that extracts of other *Dioscorea* species, generally referred to herein with *Dioscorea alata* L. cv. Phyto together as "*Dioscorea* sp." unless otherwise clear from the context, without the presence of any bone cell modulating agent, can stimulate the proliferation and differentiation of the osteoprogenitor cells so as to supplement the osteoprogenitor cells in the bone and promote maturity of osteoblastic cells and mineralization of osteoblastic cells, thereby achieving bone repair, restoration and reproduction and in turn preventing and treating osteoporosis. Moreover, the extract of the *Dioscorea alata* L. cv. Phyto, and, it is believed, other *Dioscorea* sp., not only stimulates the proliferation and differentiation of hematopoietic stem cells in bone marrow in the presence of granulocyte-macrophage colony-stimulating factor (GM-CSF), but also facilitates recovery of patients suffering from the deficiency of leukocytes and erythrocytes caused by anti-cancer drug treatment, and thus, can be used in combination with an anti-cancer drug as a chemotherapeutic adjuvant.

BRIEF SUMMARY OF THE INVENTION

An aspect of the present invention, therefore, relates to an oral composition for enhancing the proliferation and differentiation of the osteoprogenitor cells comprising, as an active component, an extract of *Dioscorea* sp.

Another aspect of the present invention relates to an oral composition for use as an anti-cancer drug adjuvant, which comprises, as an active component, an extract of *Dioscorea* sp.

A further aspect of the present invention relates to an oral composition useful for the prevention and treatment of osteoporosis.

Still a further aspect of the present invention relates to an oral composition useful as an adjuvant for the alleviation of the side effects caused by an anti-cancer drug.

Still in another aspect, the present invention relates to a method for the treatment of osteoporosis comprising administering orally to a patient in need of the treatment an effective amount of a pharmaceutically active fraction of *Dioscorea* sp.

Still in a further aspect, the present invention relates to a method for alleviation of side effects caused by chemotherapy, comprising orally administering to a patient treated with the chemotherapy an amount of a pharmaceutical composition, as a chemotherapeutic adjuvant, containing an extract of *Dioscorea* sp. effective to alleviate side effects caused by the chemotherapy.

Other features and advantages of the present invention will become apparent in the following detailed description of the preferred embodiment with reference to the accompanying drawings.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 shows bar graphs identified as FIGS. 1A and 1B.

FIG. 2 includes bar graphs identified as FIGS. 2A and 2B.

FIG. 4 includes bar graphs identified as FIGS. 4A and 4B.

FIG. 5 includes bar graphs identified as FIGS. 5A and 5B.

DETAILED DESCRIPTION OF THE INVENTION

Figure 1A:
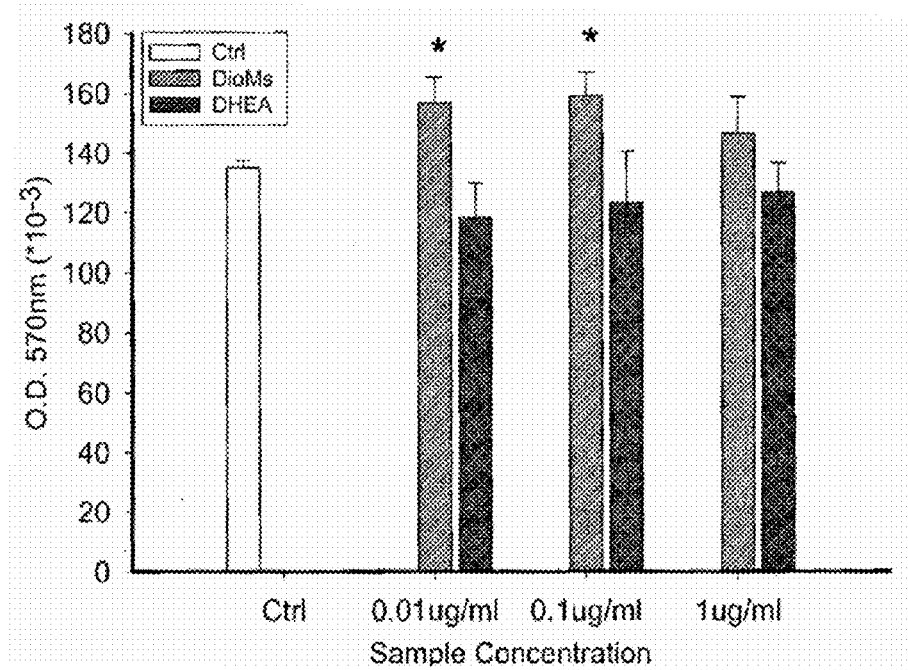
FIG. 1A illustrates the effects of the extract of *Dioscorea* sp. (DioMs) and DHEA

The present invention is based on the discovery of the biological activities of the extract of the *Dioscorea* sp., in particular the activity on cell regeneration. It was confirmed by the experiments that the methanol- or ethanol-extract and the further extracted fractions of the *Dioscorea* sp. prepared in accordance with the method of this invention include active substances that enhance the proliferation and differentiation of mouse bone marrow progenitor cells. Specifically, the methanol- or ethanol-extract and the further extracted fractions of the *Dioscorea* sp. per se enhance cell proliferation of functional osteoprogenitor cells and even extensively induce the differentiation of osteoprogenitor cells into osteoblastic cells and enhance the mineralization of osteoblastic cells. Moreover, the extract of *Dioscorea* sp. can alleviate the side-effects caused by an anti-cancer drug. Specifically, the extract restores the leukocytes and erythrocytes present in the peripheral blood of the mice treated with cyclophosphamide (CY). Therefore, the extract of the *Dioscorea* sp. would be useful in the prevention and treatment of osteoporosis, a common disease in the aging process, and may be used in combination with an anti-cancer drug as a chemotherapeutic adjuvant.

Stem cells are cells capable of self-renewal and differentiation. Stem cells are present at the maximal level during the embryonic period, and gradually decrease in number with aging. Thus, it was theorized that there is an important correlation or association between stem cells and aging. The stem cells in adults can generate a specific response toward a specific message transmitted through a microenvironment change generating new stem cells or differentiating into specific cells. When the stem cells receive a differentiation message, the stem cells rapidly reproduce in large amounts, and then finally proceed to differentiation. These stem cells are used for maintaining the balance of cells in adults, and replenish the number of cells that die due to natural causes or injuries.

The stem cells in bone marrow are divided into two types, the hematopoietic stem cells, which produce two more specialized types of stem cells, lymphoid progenitor cells (which give rise to T and B lymphocytes) and myeloid progenitor cells (which give rise to leukocytes, erythrocytes, and megakaryocytes), and stromal cells, which are the source of the cells making up the supporting structure in the bone marrow. The stromal cells have the characteristic of adhering to the bottom of plastic culture plates during culturing, and can differentiate into osteoblasts, chondrocytes, adipocytes, and even myoblasts. Stromal cells are required for the growth and differentiation of hematopoietic stem cells.

The production and number of stem cells will be greatly reduced as aging occurs, leading to various problems of aging, in which osteoporosis is the most common. The causes of osteoporosis include the loss of balance between bone formation and resorption. The osteoblastic cells derived from the osteoprogenitor cells are responsible for bone formation including the formation of the bone matrix and skeletal mineralization. Osteoprogenitor cells come from the stromal cells in the bone marrow. Dexamethasone and ascorbic acid can promote the proliferation and growth of osteoprogenitor cells, and enable the cells to differentiate into mature osteoblasts. During the differentiating process, different markers of osteoblasts are expressed: There is the deposition of collagenous matrix first, and after 10 to 14 days, alkaline phosphatase (ALP) is expressed. Alkaline phosphatase is widely used as a biochemical marker for identification of osteoblast activity, but its actual function is yet unknown, though currently it is believed that it participates in the skeletal mineralization process. After continuous culture to 21 days, the cells will secrete osteocalcein, and finally mineralize to form bone nodules.

It was unexpectedly found in this invention that an oral composition comprising a methanol or ethanol extract of the *Dioscorea* sp. or the further extracted fractions can be used to enhance the proliferation and differentiation of osteoprogenitor cells in the absence of any bone cell modulating agent, and thus, a composition comprising the active extract can be used in the treatment of osteoporosis. In one example of the invention, the *Dioscorea* sp. is *Dioscorea alata* L. cv. Phyto.

In the present invention, an oral composition for enhancing the proliferation and differentiation of cells comprises as an active component an extract of *Dioscorea* sp. that is obtained using an alcohol-based solvent as the extracting solution. The preparation process involves (a) extracting a tuber of *Dioscorea* sp. with an alcohol-based solvent in the presence of an acid, preferably in the presence of 1% acetic acid, in which the alcohol-based solvent is a methanol-based solvent, an ethanol-based solvent, or a mixture thereof.

In addition, the obtained extract may be further extracted on the basis of polarity, so as to obtain the pharmacologically active fractions. In one preferred embodiment of this invention, the extract is further subjected to partition chromatography comprising: (b) mixing a solvent mixture of ethyl acetate and water with the extract obtained from (a) so as to separate an ethyl acetate from a water extract existing in a water phase; (c) adding n-butanol solvent into the water phase to perform further extraction so as to separate a butanol extract from the remainder of water extract remaining in the water phase; and (d) adding 75% alcohol solvent into the water phase obtained from (c) to extract and further remove polysaccharide so as to obtain a purified water extract.

To confirm the biological activity of the components of *Dioscorea* sp., an analysis on the biological activity of the extract of *Dioscorea* tuber and the further extracted fractions were conducted on cells obtained from normal mice and a human patient suffering from glucocorticoid-induced osteoporosis.

Figure 1B:
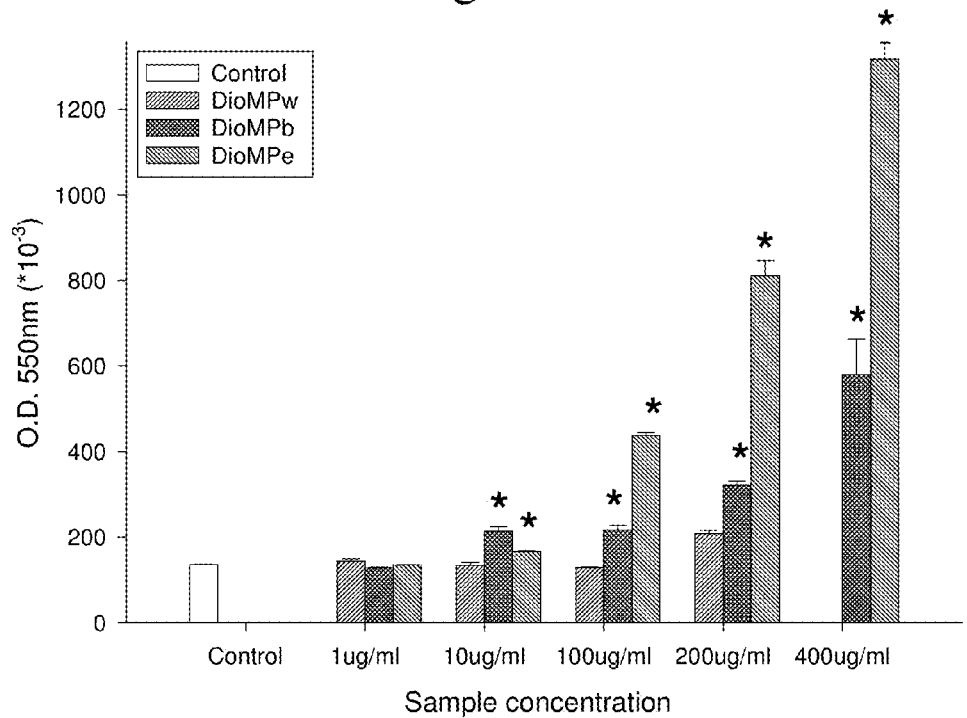
FIG. 1B illustrates the effects of each further extracted portion (DioMPw, DioMPb and DioMPe) on the proliferation of osteoprogenitor cells of C3H mice.
Figure 2A:
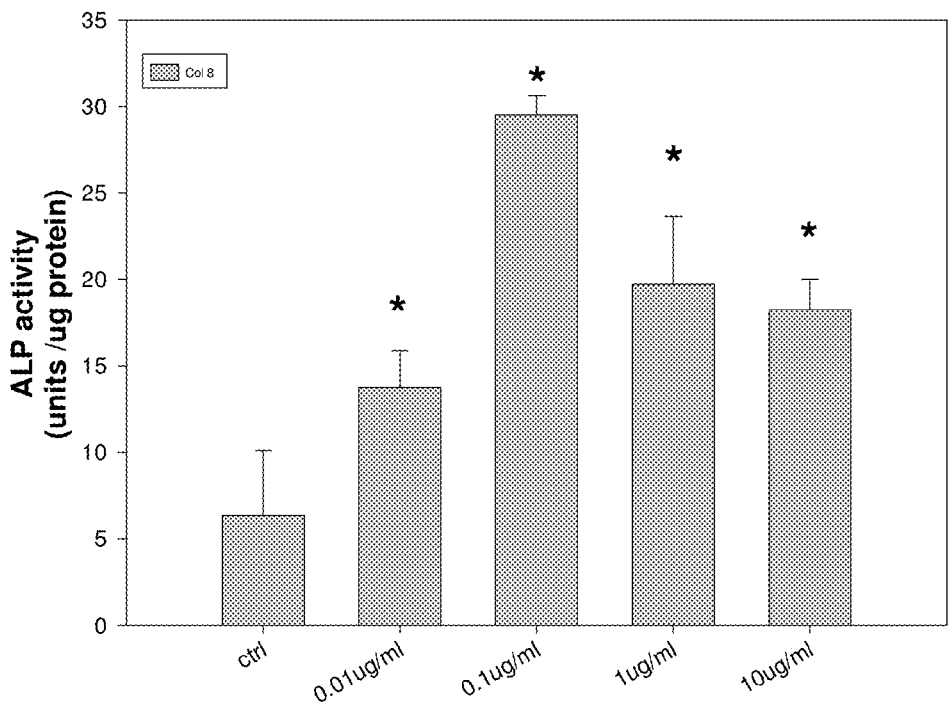
FIG. 2A shows the effects of the extract of *Dioscorea* sp.
Figure 2B:
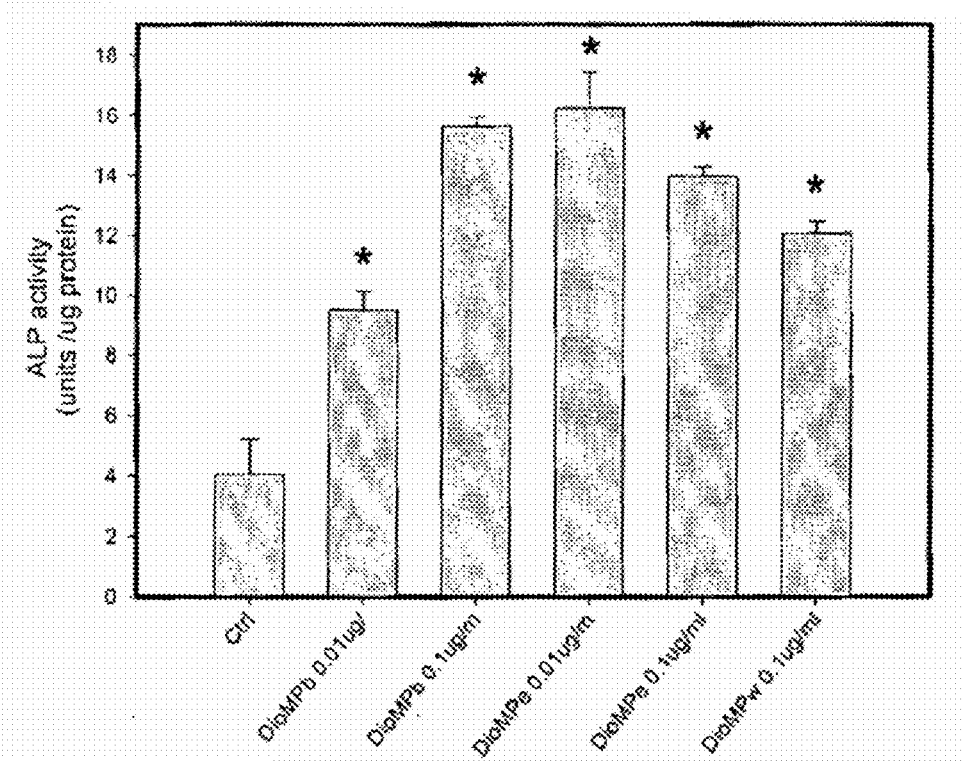
FIG. 2B illustrates the effects of each further extracted fraction on the differentiation of osteoprogenitor cells into matured osteoblastic cells of mice in vitro determined by alkaline phosphatase (ALP) activity.

From the experimental results shown in FIG. 1, it was unexpectedly found that the methanol extract of *Dioscorea* sp. and the further extracted fractions enhance the proliferation of the osteoprogenitor cells without the aid of any bone cell modulating agent. Under the same concentrations, DHEA exhibits no effect of enhancing the proliferation of osteoprogenitor cells. In FIG. 2, the results showed that the extracts of *Dioscorea* sp. significantly increase the amount of the expressed alkaline phosphatase in normal cells, that is, the extracts prepared according to the present invention can stimulate the differentiation of osteoprogenitor cells into mature osteoblastic cells.

The inventor further confirmed the effect on abnormal bone marrow cells derived from a human patient suffering from glucocorticoid-induced osteoporosis. Glucocorticoids are essential therapies for a variety of inflammatory and autoimmune diseases. However, prolonged glucocorticoid use is one of the most common iatrogenic causes of osteoporosis. Glucocorticoids may increase bone loss through a variety of effects on osteoblasts, i.e., inhibition of the replication of the osteoblastic lineage, reduction of the genesis of new osteoblastic cells and inducement of death of osteoblastic cells. From the results shown in FIG. 3, the inventor found that the active extract of the present invention increases the amount of the expressed alkaline phosphatase in such cells, and thus, the function of osteoblastic cells may be recovered by treating a patient suffering from glucocorticoid-induced osteoporosis with the active extract.

Moreover, in order to further confirm the effectiveness of the extract of *Dioscorea* sp. in treating osteoporosis in vivo, the inventor conducted experiments on normal mice and the mice that are ovariectomized to induce osteoporosis, which were orally administered the extract of the present invention.

In FIGS. 4-5, the results demonstrate that the extract of *Dioscorea* sp., in vivo, increases the amount of the expressed alkaline phosphatase and the mineralization of the osteoblastic cells derived from normal mice and ovariectomized mice. Therefore, the extract of *Dioscorea* sp. not only regulates the proliferation and differentiation of osteoprogenitor cells but also controls bone formation and remodeling, and thus, the active extract can prevent and treat osteoporosis.

It was known that the proliferation and differentiation of bone marrow cells would be governed by certain factors, such as bone morphogenetic protein-2 (BMP-2), transforming growth factor-$\beta$ (TGF-$\beta$), interluken-4 (IL-4), epidermal growth factor (EGF), granulocyte-macrophage colony-stimulating factor (GM-CSF), etc. When the factor in the culture environment is changed, the stem cells differentiate into different cells in accordance with the specificity of such factors. For example, BMP-2, TGF-$\beta$, IL-4, and EGF are positively relevant to the proliferation and differentiation of the bone marrow stromal cells toward osteoblast lineage. In this study, the inventor conducted experiments to confirm the effects of the extract of *Dioscorea* sp. on gene expression of BMP-2, TGF-$\beta$, and IL-4, and the effects of the extract and the further extracted fractions of *Dioscorea* sp. on the proliferation and differentiation of bone marrow stem cells in the presence of EGF and GM-CSF.

Figure 6:
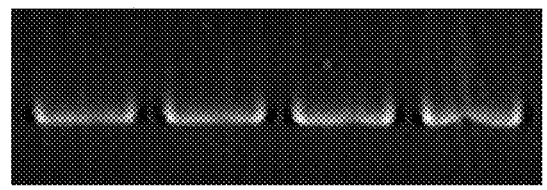
FIG. 6 shows the RT-PCR result of cytokines in bone marrow cells isolated from mice which are orally administered the extract of *Dioscorea* sp. according to the present invention.
Figure 6:
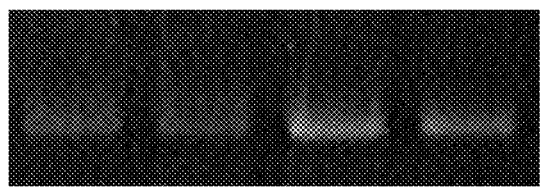
Figure 6:
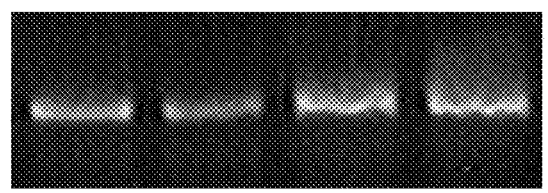
Figure 6:
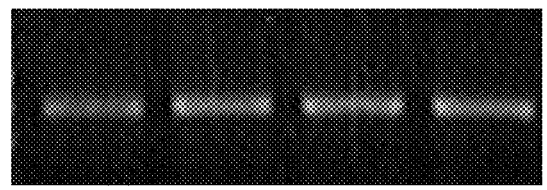
Figure 7A:
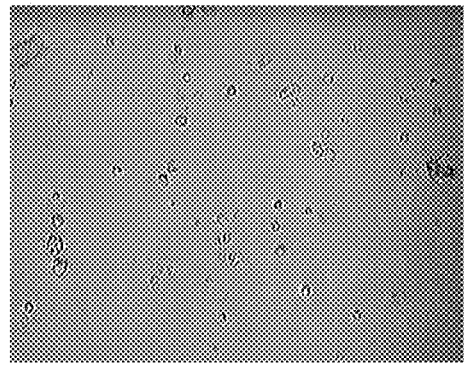
FIG. 7 consists of FIGS. 7A-7E, which are phase contrast micrograph images showing the effect of the extract of *Dioscorea* sp. on morphological changes of the primary cultured mouse bone marrow cells in the presence of epithelial growth factor (EGF)
Figure 7B:
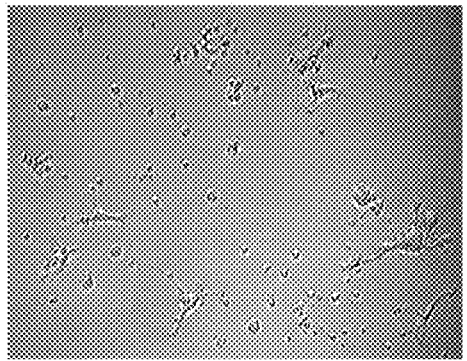
Figure 7C:
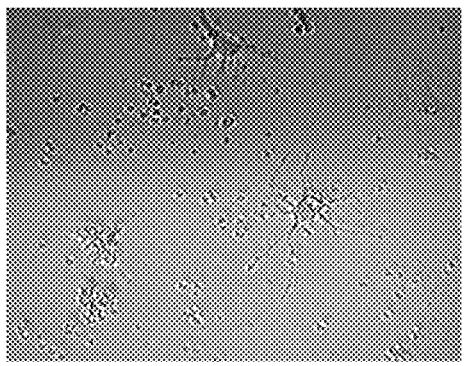
Figure 7D:
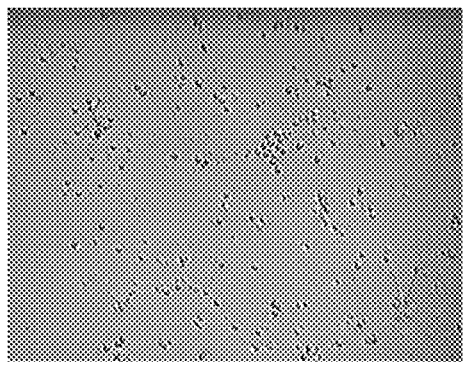
Figure 7E:
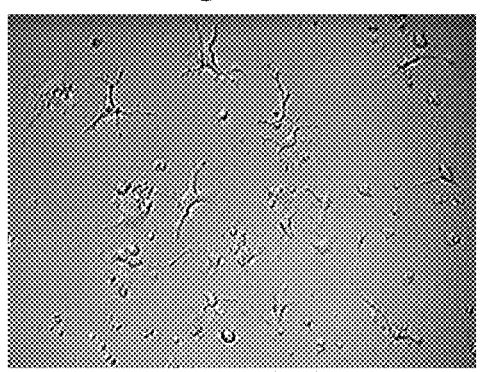

In FIG. 6, the data demonstrated that the extract of *Dioscorea* sp. increases the gene expression of BMP-2, TGF-$\beta$, and IL-4, especially that of BMP-2 and TGF-$\beta$. Moreover, from the experimental results shown in FIG. 7 and Table 2, the inventor found that the extract of *Dioscorea* sp. stimulates the differentiation of the mouse bone marrow cells in the presence of EGF. The further extracted fraction of the extract, DioMPw, enhances the proliferation of mouse bone marrow cells.

As to GM-CSF, GM-CSF can act on a specific receptor complex present on hematopoietic progenitor cells to stimulate myelopoiesis, and thus, can promote the proliferation and differentiation of the hematopoietic progenitor cells in the bone marrow into monocytes, neutrophils, macrophages, etc. Therefore, it is believed that GM-CSF has potential in therapy for restoring macrophages of a patient treated with chemotherapy. In this study, the inventor found that, in the presence of GM-CSF, the proliferation of the bone marrow cells was enhanced under the stimulation of the extract and the further extracted fractions of *Dioscorea* sp. (see Table 3 in Example 8). In addition, the results show that the differentiation of the stem cells was enhanced by the further extracted fractions of *Dioscorea* sp. Under the same conditions, DHEA exhibits the effect of enhancing cell differentiation, but cannot enhance cell proliferation. Therefore, this study suggests that the extract and the further extracted fractions of *Dioscorea* sp. prepared according to the present invention may assist GM-CSF in restoring the number of macrophages reduced by chemotherapy through the proliferation and differentiation of the bone marrow cells, and may be used as a chemotherapeutic adjuvant.

The inventor further confirmed the application of the extract of *Dioscorea* sp. with respect to chemotherapy as a chemotherapeutic adjuvant in vivo. Cyclophosphamide (CY) is a drug used to treat a number of cancers; however, it destroys the bone marrow function, decreases the blood cells such as leukocytes, macrophages, and erythrocytes, and causes many other adverse side effects. In the present invention, cyclophosphamide is employed to cause leukopenia (sometimes called leucopenia or leukocytopenia, and is a decrease in the number of white blood cells circulating in the blood) in mice to develop an animal model used to determine the function of the active extract of the present invention as a chemotherapeutic adjuvant. The obtained results showed that the active extract of the present invention prevented a decrease of leukocyte count and maintained the red blood cell count and hemoglobin content at normal level, and thus, accelerated recovery from leukopenia in CY-treated mice. Therefore, the active extract of the present invention can be used as a chemotherapeutic adjuvant to alleviate adverse side effects induced by an anti-cancer drug.

The experiments performed in accordance with the present invention clearly demonstrate that the extract of *Dioscorea* sp. and the further extracted fractions thereof enhance the proliferation and differentiation of the osteoprogenitor cells in the absence of any bone cell modulation agent, and thus, the present invention provides an application of *Dioscorea* sp. in the treatment of osteoporosis. Moreover, the extracts prepared according to the present invention increase and restore the number of the macrophages, leukocytes and erythrocytes which have been reduced by chemotherapy, and can thus be used as a chemotherapeutic adjuvant.

The term "an effective amount" used herein refers to the amount of each active agent which, upon administration with one or more other active agents to a subject in need thereof, is required to confer the therapeutic effect on the subject. The effective amount may vary, as recognized by those skilled in the art, depending on the route of administration, excipient usage, and the co-usage with other active agents, if any. According to one aspect of the invention, an effective amount refers to the amount effective in alleviating side effects caused by chemotherapy. Preferably, for this use, the dosage used in a subject is about 10 to about 1000 mg/kg/day. More preferably, for this use, the dosage is about 250 to about 500 mg/kg/day.

The carrier or excipient suitable for the pharmaceutical composition must be "acceptable" in the sense that it is compatible with the active ingredient of the composition (and preferably, capable of stabilizing the active ingredient) and not deleterious to the subject to be treated. Examples of the carriers include colloidal silicon oxide, magnesium stearate, cellulose, sodium lauryl sulfate, D&C Yellow #10, microcrystalline cellulose, mannitol, glucose, defatted milk powder, polyvinylpyrrolidone, and starch, or a combination thereof. The pharmaceutical composition, when in an oral administrable form, may be in a variety of forms, such as tablet, capsule, powder, or liquid.

According to the invention, the above-mentioned composition may be administered via suitable routes, e.g., oral administration. A solid formulation for oral administration may contain suitable carriers or excipients, such as corn starch, gelatin, lactose, acacia, sucrose, microcrystalline cellulose, magnesium stearate, talc, croscarmellose sodium, kaolin, mannitol, dicalcium phosphate, calcium carbonate, sodium chloride, or alginic acid. This solid formulation may be designed to be released in the intestine. For example, the composition is confined in a solid sub-unit or a capsule compartment that have respectively a matrix or a wall or a closure comprising an enteric polymer which dissolves or disperses at the pH of the small or large intestine to release the drug substance in the intestine.

In another example, the extract of *Dioscorea* sp. and the further extracted fractions thereof described herein is a component of a food product or a food supplement (e.g., a nutrient supply or an herbal product). Such food products may be prepared by any standard or commonly used methods in the food industry.

The following examples are provided to illustrate the present invention. The examples are not intended to limit the scope of the present invention and they should be so interpreted.

EXAMPLES OF THE INVENTION

Preparatory Step 1

Preparation of a Methanol Extract of *Dioscorea* sp.

Four (4) kg peeled tubers of *Dioscorea alata* L. cv. Phyto. were immersed in 1% (v/v) acetic acid solution overnight. The solid portion obtained was then frozen at −70° C. and lyophilized. The lyophilized portion was immersed in methanol in the presence of 1% acetic acid. After stirring and adjusting the concentration of methanol to 40% by volume, the mixture solution was allowed to stand overnight, and then separated by centrifugation. The obtained soluble fraction was lyophilized and is referred to as DioMs.

DioMs was further subjected to partition chromatography, comprising the steps of: using a solvent mixture of ethyl acetate and water (1:1) to extract DioMs so as to separate an ethyl acetate extract (referred as DioMPe) from a water extract existing in the water phase; adding n-butanol solvent into the water phase to perform further extraction so as to separate an butanol extract (referred as DioMPb) from the water extract remaining in the water phase; and adding 75% (v/v) alcohol solvent into the water phase to extract and further remove polysaccharide so as to obtain a purified water extract (referred as DioMPw).

Preparatory Step 2

Preparation of a Feed for Mice Containing a Methanol Extract of *Dioscorea* sp.

Purina Chow 5001, a commercially available mouse feed, was ground into powder. The lyophilized methanol extract of *Dioscorea alata* L. cv. Phyto was added in the ground feed in an amount to replace the same amount from the ground feed, to form a feed mixture. The feed mixture was uniformly mixed with distilled water, re-shaped by extrusion molding, baked for 2 min. in a microwave oven at proper power, and refrigerated at −70° C. after cooling to room temperature. After lyophilization, the feed mixture was formed into pellets very similar to the properties of the Purina Chow feed. The formed pellets were stored in a −20° C. refrigerator. The pellets were warmed to room temperature on the day of feeding, and were sterilized by UV lamp irradiation on a sterile work table. Feed mixtures having different concentrations of methanol extract were prepared.

Preparatory Step 3

Isolation and Culture of Bone Marrow Cells

Under sterile conditions, specific pathogen-free (SPF) grade C3H/HeN mice were sacrificed and their femoral bones were injected with a liquid culture of Dulbecco's Modified Eagle Medium (DMEM)/F12 to flush out the bone marrow cells. The cells were filtered through sterile No. 53 nylon mesh. The single cell suspension so obtained was mixed with DMEM/F12 culture medium containing $N_2$ to adjust to the proper concentration.

Preparatory Step 4

Preparation of Osteoprogenitor Cells from Mice

Under sterile conditions, femoral bones of the SPF grade of C3H/HeN mice were obtained and injected with DMEM/F12. The bone marrow cells were flushed out and filtered through No. 53 sterile nylon mesh. The single cell suspension obtained was mixed with DMEM/F12 culture medium containing 15% FCS to adjust the concentration of the cells.

The cells were cultured in DMEM/F12 medium containing 15% FCS, 50 µg/ml ascorbic acid, 10 mM sodium β-glycerophosphate and 10 nM dexamethasone in a T-flask for 6 days. The culture medium was renewed every 3 days. The cell concentration was $10^6$ cells/cm$^2$. On the $6^{th}$ day, the suspended cells and culture medium were drawn out. The adhering cell layer was washed with 1×PBS that had been warmed to room temperature, and then treated with 0.01% EDTA at 37° C. for 5 to 10 minutes. The EDTA was removed and the reaction was stopped in a culture medium containing fetal calf serum (FCS). The cells were all collected and centrifuged for 5 minutes at 1000 rpm.

Example 1

The Proliferative Response of Osteoprogenitor Cells of Mice Treated with the Methanol Extract and the Further Extracted Fractions of *Dioscorea* sp.

The cells obtained in Preparatory Step 4 were dispersed using a 22G gauge needle and suspended in DMEM/F12 medium containing 15% FCS, 50 µg/ml ascorbic acid, 10 mM sodium β-glycerophosphate and 10 nM dexamethazone to form a concentration of 4.5×10$^4$ cells/ml. 225 µl cell suspension was added into each well of a 96-well microplate. After 3 hours, to the cell suspension in each well was added 25 µl methanol extract, each of the further extracted fractions and dehydroepiandrosterone (DHEA) and incubated for 72 hours. Then, 3-(4,5-dimethylthiazol-2-yl)-2,5-diphenyltetrazolium bromide (MTT) assay was performed. 1 mg/ml MTT solution was added in each well and reacted for 4 hours. MTT lysis buffer (20% sodium dodecyl sulfate (SDS)-50% dimethyl formamide (DMF)) was added in each well in the amount of 150 µl/well and reacted for 16 hours, and the absorbance was measured at O.D. 570 nm for the resultant cell suspension in each well.

As shown in FIG. 1, under the stimulation of the methanol extract of *Dioscorea* sp., the proliferation of the osteoprogenitor cells was enhanced, in which the 0.01 and 0.1 µg/ml concentrations manifest significant enhancing effect. Under the same concentrations, DHEA exhibits no effect of enhancing the proliferation of osteoprogenitor cells. The extracted fractions, DioMPe and DioMPb, enhance cell proliferation at 10-400 µg/ml, wherein DioMPe exhibits an excellent effect.

Example 2

The Effect of the Methanol Extract and Different Extracted Fractions of *Dioscorea* sp. on the Differentiation of Matured Osteoblastic Cells of Mice Determined by Alkaline Phosphatase Activity (ALP) In Vitro Osteoprogenitor cells collected in Preparatory Step 4 were incubated in a T-flask for 6 days. The cells were dispersed with 22G gauge needle, and the cell concentration was adjusted to 5×10$^3$ cell/cm$^2$. The cells were then incubated in 6-well plates, in which 4.5 ml of cell culture medium was added in each well, and 0.5 ml methanol extract and each of the extracted fractions were added the next day. After incubation for 14 days, alkaline phosphatase activity assay was conducted thereon, as described below.

Drawing out the culture medium, the cell layer was washed several times with PBS. 0.5% Triton® X-100 in PBS was added into each well. The resultant suspension was subjected to a freezing and thawing process at a temperature of −70° C. and 37° C., respectively. The treatment was done twice so as to obtain a test sample. 50 µl of the test sample was transferred from each well to an ELISA plate. 50 µl AMP-substrate buffer (2-amino-2-methyl-1-propanol (AMP, 0.5 M) in distilled water, pH 10; 2 mM magnesium chloride and 9 mM p-nitrophenyl phosphate) was then added into the ELISA plate so as to be reacted with the test sample at room temperature for 10-20 min. Immediately after the absorbance was measured at 410 nm wavelength using ELISA reader, the protein concentration of each well was measured quantitatively. The measure alkaline phosphatase activity is expressed in unit/µg.

As shown in FIG. 2, after 14 days of incubation of the bone marrow precursor cells, expression of alkaline phosphatase, which is the expressed marker specific to a matured osteoblast, was noted. The methanol extract of *Dioscorea* sp. and each of further extracted fractions of the methanol extract significantly increase the amount of the expressed alkaline phosphatase, in which the methanol extract at 0.1 µg/ml, DioMPb at 0.1 µg/ml, DioMPe at 0.01-0.1 µg/ml, and DioMPw at 0.1 µg/ml showed the strongest enhancement effect.

Example 3

The Effects of the Methanol Extract *Dioscorea* sp. on Alkaline Phosphatase (ALP) Activity of Bone Marrow Cells Derived from a Patient Suffering from Glucocorticoid-Induced Osteoporosis The patient's bone marrow cells obtained from the Taipei Veterans General Hospital were cultured in DMEM/F12 medium containing 15% FCS, 50 µg/ml ascorbic acid, 10 mM sodium β-glycerophosphate and 10 nM dexamethasone for 7 days. Alkaline phosphatase activity assay was conducted thereon.

Figure 3:
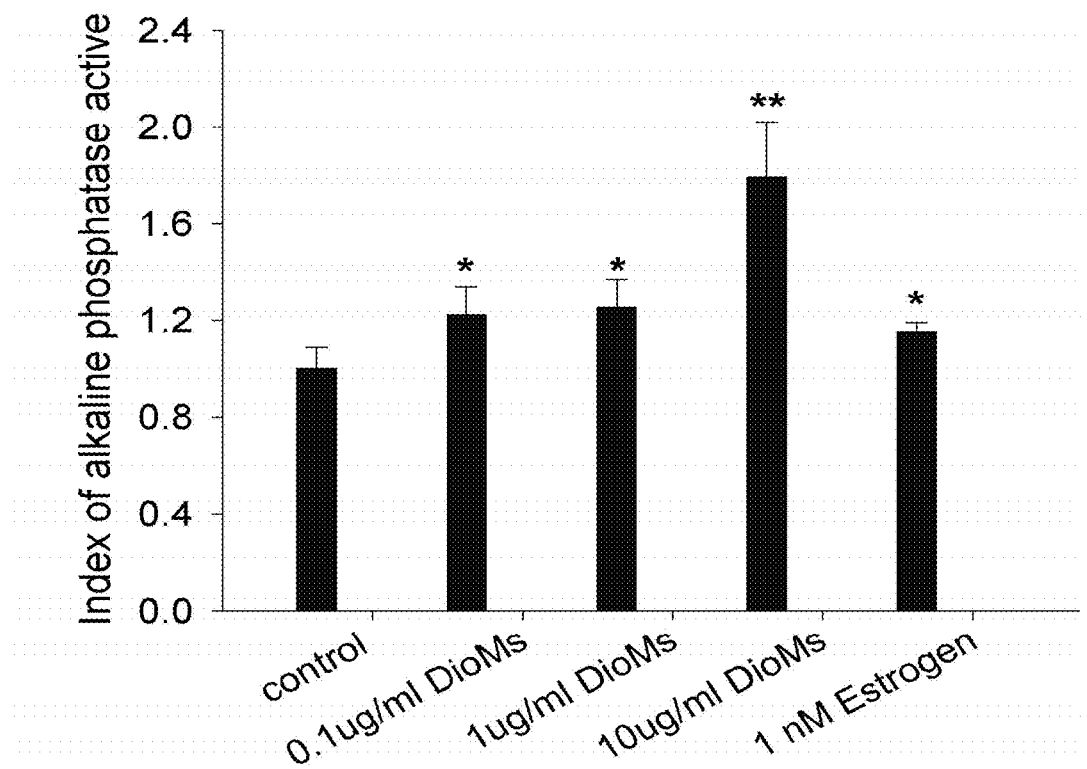
FIG. 3 is a bar graph showing the in vitro effects of the extract of *Dioscorea* sp. on alkaline phosphatase (ALP) activity of the bone marrow cells derived from a patient suffering from glucocorticoid-induced osteoporosis.

As shown in FIG. 3, expression of alkaline phosphatase was noted. Compared with the control group and positive group (1 nM estrogen, which is the known treatment for osteoporosis), the methanol extract of *Dioscorea* sp. increased the amount of the expressed alkaline phosphatase, in which the methanol extract at 10 µg/ml showed the strongest enhancement effect.

Example 4

The Effects of Methanol Extract of *Dioscorea* sp. on Alkaline Phosphatase (ALP) Activity and on Mineralization of Bone Marrow Cells In Vivo Different dosages (0, 40, 200, and 1000 mg/kg) of methanol extract were prepared for oral administration. After oral administration of different dosages of the methanol extract for 5 days, mice were sacrificed to obtain marrow cells thereof.

(1) Alkaline Phosphatase Activity Assay

The bone marrow cells of mice obtained were cultured in 96-well microplates at $2\times10^5$ cells/well, in which 250 µl of α-minimum essential medium (MEM) containing 15% FCS, 50 µg/ml ascorbic acid, 10 mM sodium β-glycerophosphate and 10 nM dexamethasone was added, and incubated in a 5% $CO_2$ incubator at 37° C. for 2 days. 125 µl/well of culture medium was drawn out and replaced by 125 µl/well of fresh medium containing 15% FCS, 50 µg/ml ascorbic acid, 10 mM sodium β-glycerophosphate, and 10 nM dexamethasone. After 4 days incubation, an alkaline phosphatase activity assay was conducted thereon.

Figure 4A:
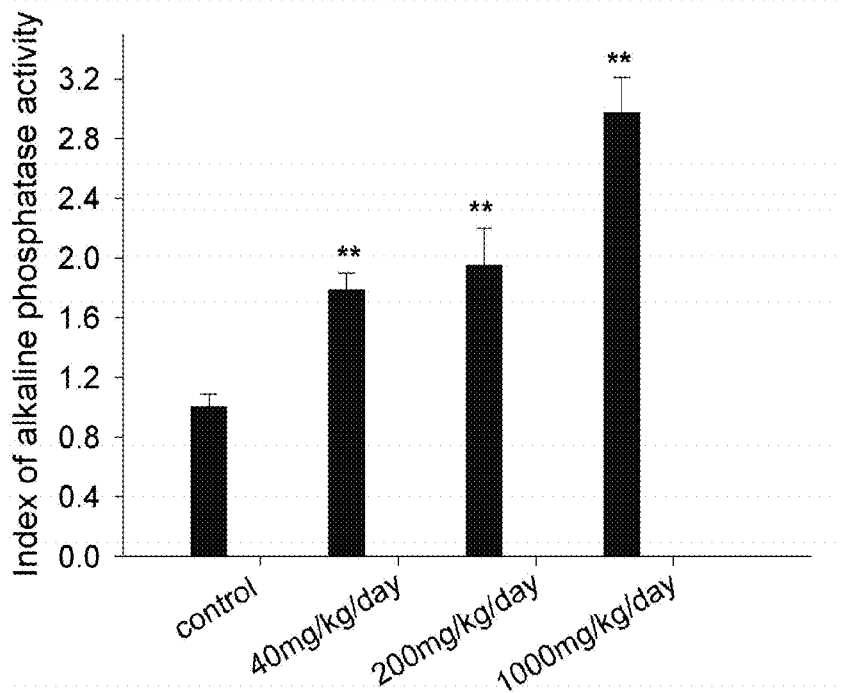
FIG. 4A shows the in vivo effects of the extract of *Dioscorea* sp. on the differentiation of osteoprogenitor cells into matured osteoblastic cells of mice determined by alkaline phosphatase (ALP) activity.

As shown in FIG. 4A, expression of alkaline phosphatase was noted. In FIG. 4A, the methanol extract of *Dioscorea* sp. increases the amount of the expressed alkaline phosphatase, in which the methanol extract at 1000 mg/kg reaches up to 3 times enhancement as compared with the control group.

(2) Nodule Formation Assay

This assay is used to analyze the mineralization of the bone mass. The bone marrow cells obtained from the mice orally administered different dosages (0, 40, 200, and 1000 mg/kg) of methanol extract were seeded in 24-well plates at $1\times10^6$ cells/well, cultured in α-MEM medium containing 15% FCS, 50 µg/ml ascorbic acid, 10 mM sodium β-glycerophosphate and 10 nM dexamethasone, and incubated in a 5% $CO_2$ incubator at 37° C. for 24 hrs. 500 µl/well of culture medium was drawn out and replaced by 500 µl/well of fresh medium containing 15% FCS, 50 µg/ml ascorbic acid, 10 mM sodium β-glycerophosphate and 10 nM dexamethasone. The cells were further incubated for 15 days to analyze the mineralization of the bone mass, and the culture medium renewed every 4 days. Nodule formation assay was conducted thereon, as described below.

Drawing out the culture medium, the cells were fixed by reacting them with 500 µl/well formalin for 30 minutes in a 5% $CO_2$ incubator at 37° C. After removing formalin and rinsing the cells with sterilized water three times, 200 ∥l/well of 2% Alizarine Red S solution, which reacts with calcium, was added into the wells and the cells were further incubated in a 5% $CO_2$ incubator at 37° C. for 10 minutes. Then, the Alizarine solution was removed and the cells were rinsed three times with absolute alcohol. The mineralized area of the bone mass was measured by Meta Image.

Figure 4B:
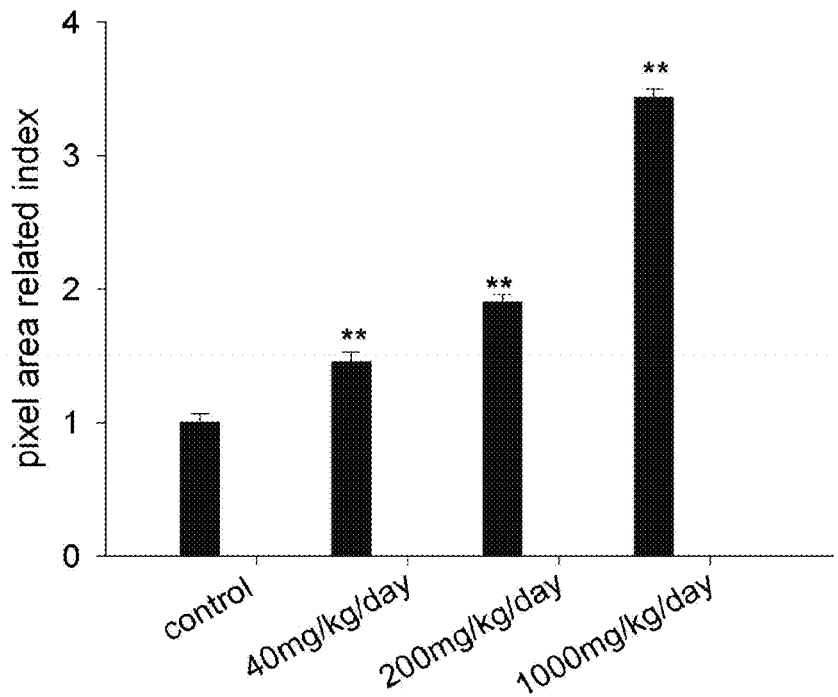
FIG. 4B shows the effects of the extract on the mineralization of the bone mass in the bone marrow cells of the healthy mice determined by the nodule formation.

As shown in FIG. 4B, compared with the control group, the methanol extract of *Dioscorea* sp. promotes mineralization of the bone mass, in which the methanol extract at 1000 mg/kg dosage showed the strongest enhancement effect of up to 3.5 times.

Example 5

The Effect of the Methanol Extract of *Dioscorea* sp. on Alkaline Phosphatase (ALP) Activity and on Mineralization of Bone Marrow Cells in Ovariectomized Mice Model Under sterile conditions, a group of SPF grade C57BL/6j mice were subjected to a surgical operation to remove their ovaries so as to induce the occurrence of osteoporosis and another group was merely operated on without removal of the ovary for use as a control group (referred to as pseudo operated mice).

Different dosages (0, 40, 200, and 1000 mg/kg) of methanol extract were prepared for oral administration. After being orally administered with different dosages of the methanol extract for 42 days, the mice were sacrificed to obtain bone marrow cells thereof.

(1) Alkaline Phosphate Activity Assay

The bone marrow cells obtained from the mice orally administered different dosages (0, 40, 200, and 1000 mg/kg) of methanol extract and the pseudo operated mice were cultured in 96-well microplate at $2\times10^5$ cells/well, in which 250 µl of α-MEM medium containing 15% FCS, 50 µg/ml ascorbic acid, 10 mM sodium β-glycerophosphate and 10 nM dexamethasone were added, and incubated in a 5% $CO_2$ incubator at 37° C. for 2 days. 125 µl/well of fresh medium containing 15% FCS, 50 µg/ml ascorbic acid, 10 mM sodium β-glycerophosphate and 10 nM dexamethasone was added. After 4 days incubation, an alkaline phosphatase activity assay was conducted thereon.

Figure 5A:
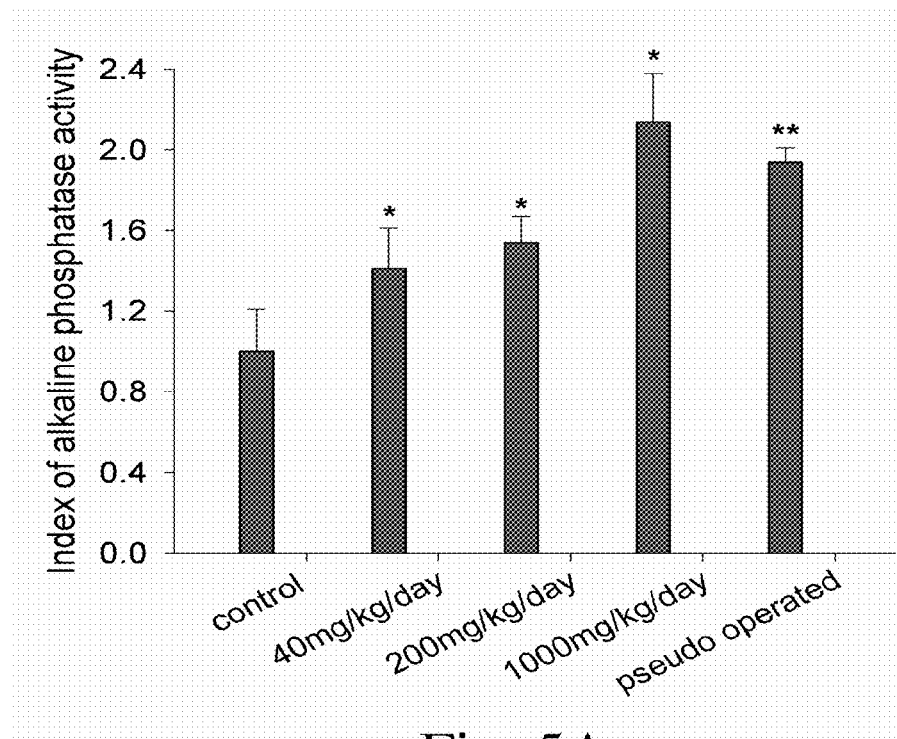
FIG. 5A shows the in vivo effects of the extract of *Dioscorea* sp. on alkaline phosphatase (ALP) activity.

As shown in FIG. 5A, expression of alkaline phosphatase was noted. In FIG. 5A, the methanol extract of *Dioscorea* sp. is shown to increase the amount of the expressed alkaline phosphatase, in which the methanol extract at 1000 mg/kg showed the strongest enhancement effect.

(2) Nodule Formation Assay

The bone marrow cells obtained from the mice orally administered different dosages (0, 40, 200, and 1000 mg/kg) of methanol extract were seeded in 24-well plates at $1\times10^6$ cells/well, cultured in α-MEM medium containing 15% FCS, 50 µg/ml ascorbic acid, 10 mM sodium β-glycerophosphate and 10 nM dexamethasone, and incubated in a 5% $CO_2$ incubator at 37° C. for 24 hrs. 500 µl/well of culture medium was drawn out and replaced by 500 µl/well of fresh medium containing 15% FCS, 50 µg/ml ascorbic acid, 10 mM sodium β-glycerophosphate and 10 nM dexamethasone. The cells were further incubated for 15 days to analyze the mineralization of the bone mass, and the culture medium renewed every 4 days. A nodule formation assay was conducted thereon.

Figure 5B:
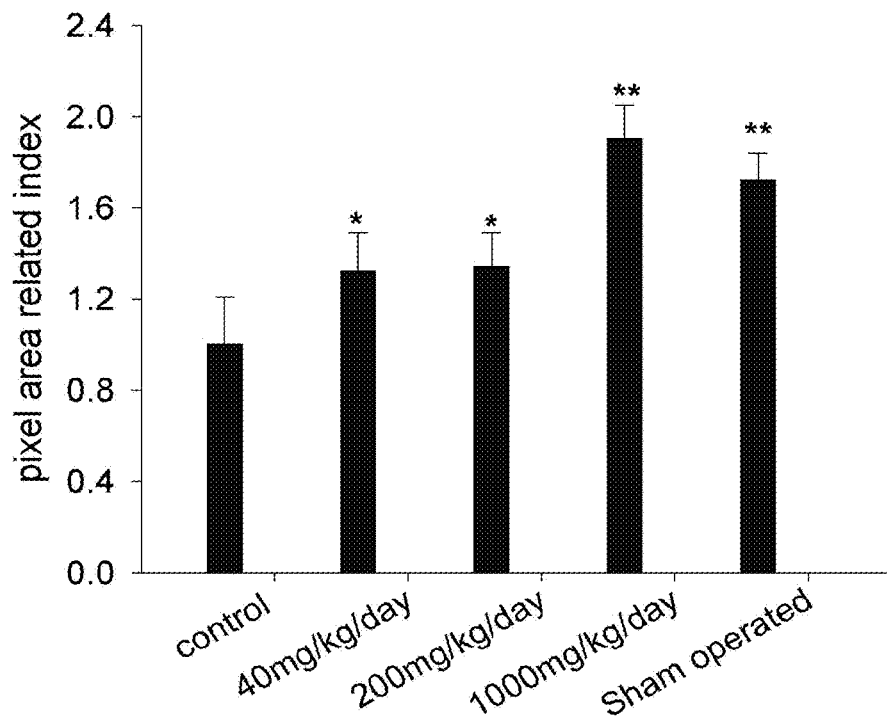
FIG. 5B shows the effects of the extract on the mineralization of the bone mass in the bone marrow cells of ovariectomized mice.

As shown in FIG. 5B, compared with the control group, the methanol extract of *Dioscorea* sp. promotes mineralization of the bone mass, in which the methanol extract at 1000 mg/kg showed the strongest enhancement effect.

Example 6

The Effect of the Methanol Extract *Dioscorea* sp. on Gene Expression of Cytokines in the Bone Marrow Cells Total RNA was extracted from the bone marrow cells obtained from Example 4 using an Ultraspec™ RNA isolation kit (Biotex Laboratories Inc, U.S.A.). 5 µg total RNA and 2.5 µg oligo dT were heated at 70° C. for 10 minutes, cooled to room temperature for 10 minutes, then added with 4 µl 10 mM dNTP, 0.5 µl rRNasin, 1 µl (10 units) AMV (Avian Myeloblastosis virus) reverse transciptase and the buffer thereof, and the final reaction volume was 26.5 µl. The cDNA was obtained by reacting the previous reaction solution at 42° C. for 60 minutes and then at 90° C. for 5 minutes. 2.5 µl resultant cDNA was added with 0.5 µl 10 mM dNTP, 0.5 µl polymerase (2 units) and the buffer thereof, 1 µl of 10 µM targeted primers, and the final volume of the reaction mixture was 25 µl. PCR was performed for proper cycles, each cycle consisting of 45 seconds of denaturation at 94° C., 45 seconds of annealing at proper annealing temperature and 1 min of extension at 72° C. The reaction products were visualized by electrophoresis in 2% agarose gel. Sequences of the PCR primers are shown in Table 1. The experimental results are shown in FIG. 6.

As shown in FIG. 6, the gene expression of bone morphogenetic protein (BMP)-2, TGF-β, and IL-4 increased, especially BMP-2 and TGF-β.

TABLE 1

Sequences of the primers used in RT-PCR

| Cytokine | Sequence (5' to 3') | | [a] Size (bp) |
|---|---|---|---|
| IL-4 | | | |
| sense | ATG GGT CTC AAC CCC CAG CTA GT | (SEQ ID NO: 1) | 339 |
| antisense | GCT CTT TAG GCT TTC CAG GAA GTC | (SEQ ID NO: 2) | |
| TGF-β | | | |
| sense | TGG ACC GCA ACA ACG CCA TCT ATG CCA TCT ATG AGA AAA CC | (SEQ ID NO: 3) | 525 |
| antisense | TGG AGC TGA AGC AAT AGT TGG TAT CCA GGG CT | (SEQ ID NO: 4) | |
| BMP-2 | | | |
| sense | CAT CCA GCC GAC CCT TG | (SEQ ID NO: 5) | 505 |
| antisense | CTC TCC CAC TGA CTT GTG | (SEQ ID NO: 6) | |
| B-actin | | | |
| sense | GAC TAC CTC ATG AAG ATC CT | (SEQ ID NO: 7) | 510 |
| antisense | CA CAT CTG CTG GAA GGT GG | (SEQ ID NO: 8) | |

[a] The size of cytokine marker was determined by polymerase chain reaction (PCR) using the primers with reference to a 100 bp DNA ladder.

Example 7

Effects of Methanol Extract of *Dioscorea* sp. on Morphological Changes of Bone Marrow Cells of C3H Mice in the Presence of Epithelial Growth Factor (EGF)

1×10$^4$ cells/well bone marrow cells of mice obtained in Preparatory Step 3 were seeded in a 96-well microplate containing DMEM/F12 culture medium with N$_2$ and 10 ng/ml EGF and incubated in a 5% CO$_2$ incubator at 37° C. for 24 hrs. The extract and DHEA were added into different wells respectively. Wells containing pure culture medium into which no methanol extract and DHEA were added, and which were subjected to the same incubation procedure, were used as positive control. In addition, for use as positive control, the same procedure as that for control was repeated except that 50 ng/ml EGF was used. The proliferation responses were measured by a MTT assay. In accordance with the MTT assay, each of the wells was added with 1 mg/ml MTT solution and, after 4 hours of reaction, MTT lysis buffer (20% SDS-50% DMF) was added thereinto in an amount of 150 μl/well. The resultant mixture was allowed to be reacted for 16 hours. The absorbance was measured at O.D. 570 nm.

As shown in FIG. 7, in the event that the progenitor cells in bone marrow induced with EGF proliferate, the methanol extract of *Dioscorea* sp. was found to further stimulate the bone marrow progenitor cells to differentiate significantly. It can be noted that a more desirable optimum result was obtained when the concentration of the methanol extract used was at 10 μg/ml. It is further shown in Table 2 that when 10 μg/ml of DioMPw was used as stimulation, the cells exhibited significantly enhanced proliferative effect. Where that 100 μg/ml of DioMPw were used, the proliferation rate of the cell might reach up to 1.9 times that of the control as manifested in Table 2.

TABLE 2

| Group | Concentration | Proliferation Index[a] | Morphologic Change[b] |
|---|---|---|---|
| Control | | 1.00 | + |
| DHEA | 0.0001 μg/ml | 0.99 | + |
| | 0.001 μg/ml | 0.64 | + |
| | 0.01 μg/ml | 0.65 | + |
| | 0.1 μg/ml | 0.67 | ++ |
| | 1 μg/ml | 0.70 | ++ |
| DioMPw | 10 ng/ml | 1.09 | − |
| | 100 ng/ml | 1.13 | − |
| | 1 μg/ml | 1.17 | − |
| | 10 μg/ml | 1.34* | − |
| | 100 μg/ml | 1.90* | − |

[a] Data were analyzed by Student's t-test, and "*" means P < 0.05
[b] Morphologic change was observed by microscope.

Example 8

The Proliferation Response of Bone Marrow Cells of Mice Treated with Methanol Extract and the Further Extracted Fractions of *Dioscorea* sp. in the Presence of GM-CSF 1×10$^4$ cells/well bone marrow cells of mice obtained in preparatory step 3 were seeded in each well of the 96-well microplate, cultured in DMEM/F12 culture medium containing N$_2$, and 4 ng/ml mGM-CSF (granulocyte monocyte colony stimulating factor). Methanol extracts of *Dioscorea* sp. with different concentrations were respectively added into the resultant cultured cells in the different wells. The resultant methanol extract containing cultured cells in different wells were then incubated in a 5% CO$_2$ incubator at 37° C. for 14 days. The cells cultured in DMEM/F12 medium containing N$_2$ and 20 ng/ml mGM-CSF is used as positive control. A MTT assay was performed. In this respect, 1 mg/ml MTT solution was added in each well so as to react with the cultured cells therein for 4 hours. MTT lysis buffer (20% SDS-50% DMF) was added in a n amount of 150 μl/well. The resultant mixture was allowed to react for 16 hours. The absorbance was measured at O.D. 570 nm.

As shown in Table 3, under the stimulation of the methanol extract of *Dioscorea* sp. in concentrations ranging from 0.001 μg/ml to 1000 μg/ml, the fractions resulting from further extraction of the methanol extract are all found to have the ability to enhance cell proliferation. Among them, DioMPb and DioMPe were particularly found to have excellent effect on the enhancement of proliferation. In addition, the 20-week adult mouse bone marrow cells were found to be able to differentiate upon stimulation by the methanol extract of *Dioscorea* sp. at concentrations of 1 μg/ml-10 μg/ml. Among the extracted fractions of the methanol extract, which were extracted by a solvent mixture of water and ethyl acetate extracted fraction and the 75% alcohol extracted fraction resulting from further extracting the water extract with the 75% alcohol, are found to accelerate the differentiation of 20-week old adult mouse bone marrow cells. Under the same conditions, however, DHEA, in contrast, exhibits only the effect of enhancing cell proliferation. Therefore, the extracts of *Dioscorea* sp. which exhibit excellent effect on both the regeneration and differentiation of stem cells may assist GM-CSF in restoring the number of macrophages reduced by chemotherapy, and may be used as a chemotherapeutic adjuvant.

TABLE 3

| Group | Concentration | Proliferation Index[a] | Morphologic Change[b] |
| --- | --- | --- | --- |
| Control | | 1.00 | + |
| DioMs | 0.0001 μg/ml | 1.08 | + |
| | 0.001 μg/ml | 1.19* | + |
| | 0.01 μg/ml | 1.68* | + |
| | 0.1 μg/ml | 1.95* | + |
| | 1.0 μg/ml | 1.78* | ++ |
| | 10 μg/ml | 1.82* | +++ |
| | 100 μg/ml | 1.49* | + |
| | 1000 μg/ml | 1.39* | + |
| DioMPe | 0.01 μg/ml | 0.98 | + |
| | 0.1 μg/ml | 1.11 | ++ |
| | 1 μg/ml | 1.35* | ++ |
| | 10 μg/ml | 2.64* | +++ |
| | 100 μg/ml | 0.83 | –[c] |
| | 300 μg/ml | 0.97 | – |
| DioMPb | 0.01 μg/ml | 1.07 | + |
| | 0.1 μg/ml | 1.23 | + |
| | 1 μg/ml | 1.34 | + |
| | 10 μg/ml | 1.41 | + |
| | 100 μg/ml | 1.90* | + |
| | 300 μg/ml | 2.02* | + |
| DioMPw | 0.0001 μg/ml | 1.06 | + |
| | 0.001 μg/ml | 1.08 | + |
| | 0.01 μg/ml | 1.12 | ++ |
| | 0.1 μg/ml | 1.18 | ++ |
| | 1.0 μg/ml | 1.31* | +++ |

TABLE 3-continued

| Group | Concentration | Proliferation Index[a] | Morphologic Change[b] |
| --- | --- | --- | --- |
| | 10 μg/ml | 1.56* | + |
| DHEA | 0.0001 μg/ml | 0.99 | + |
| | 0.001 μg/ml | 1.15 | + |
| | 0.01 μg/ml | 1.04 | + |
| | 0.1 μg/ml | 1.13 | + |
| | 1 μg/ml | 1.11 | +++ |
| | 10 μg/ml | 1.19* | + |

[a]Data were analyzed by Student's t-test, and means $P < 0.05$
[b]Morphologic change was observed by microscope.
[c]Bone marrow cells were found dead under high concentration of DioMPe.

Example 9

The Effect of the Methanol Extract of *Dioscorea* sp. on the Number of Leukocyte and Red Blood Cells and Hemoglobin Content in Peripheral Blood of Leukopenia Mice Induced by Cyclophosphamide Different dosages (0, 20, 100, and 500 mg/kg) of methanol extract of *Dioscorea* sp. were prepared for oral administration. The mice were intraperitoneally injected with 200 and 100 mg/kg of cyclcophosphamide (CY) on day 0 and day 5 to cause leukopenia, and blood was drawn periodically to cause an anemia condition. The mice were orally administered different dosages of the methanol extract on day 1 until the mice were sacrificed. The peripheral blood collected from the retro-orbital sinus was sampled on days 0, 4, 8, and 12.

The blood (0.1 ml) obtained on days 0, 4, 8, and 12 was added with 25 μl EDTA solution (72 mg/ml) to prevent blood coagulation, and diluted 10× or 20× with Turk's solution (2% acetic acid with 0.01% crystal violet). The number of leukocytes were counted by microscope.

To the blood (0.1 ml) obtained on day 8 was added 25 μl EDTA solution (72 mg/ml) to prevent blood coagulation, and diluted 2000× with saline. The number of erythrocytes was counted. Hemoglobin (Hbg) content was determined as described by Worthington, R. E. et al., *Experimental Hematology*, 15:85-92, 1987.

Figure 8:
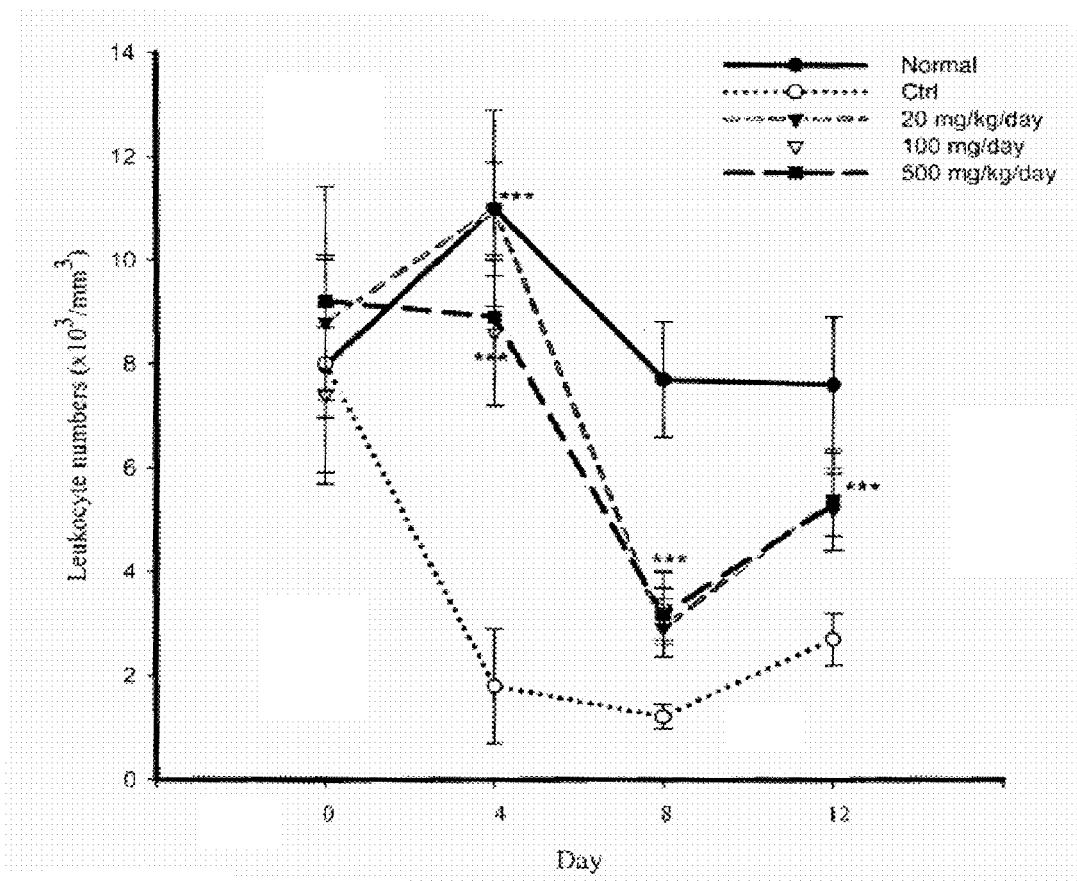
FIG. 8 is a graph that shows the in vivo effect of the extract of *Dioscorea* sp. on the leukocyte count in the peripheral blood of leucopenia mice induced by cyclophophamide (CY)
Figure 9:
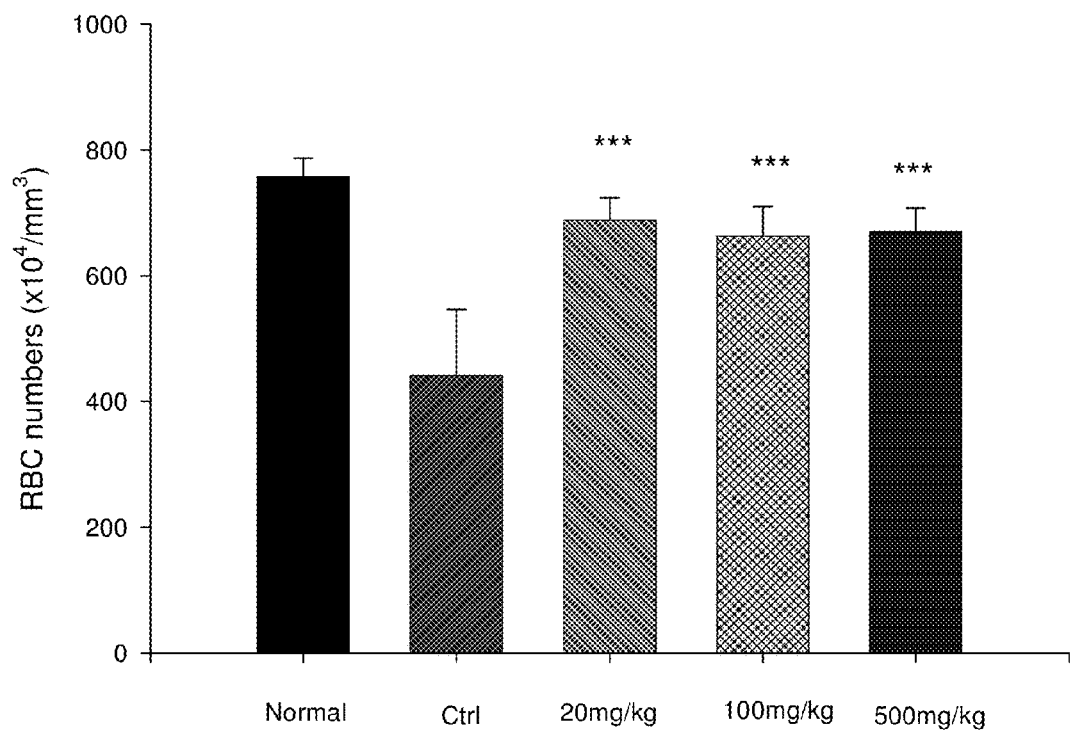
FIG. 9 is a bar graph showing the in vivo effect of the extract of *Dioscorea* sp. on red blood cell (RBC) count in the peripheral blood of cyclophosphamide (CP)-induced leukopenic mice suffering from severe anemia.
Figure 10:
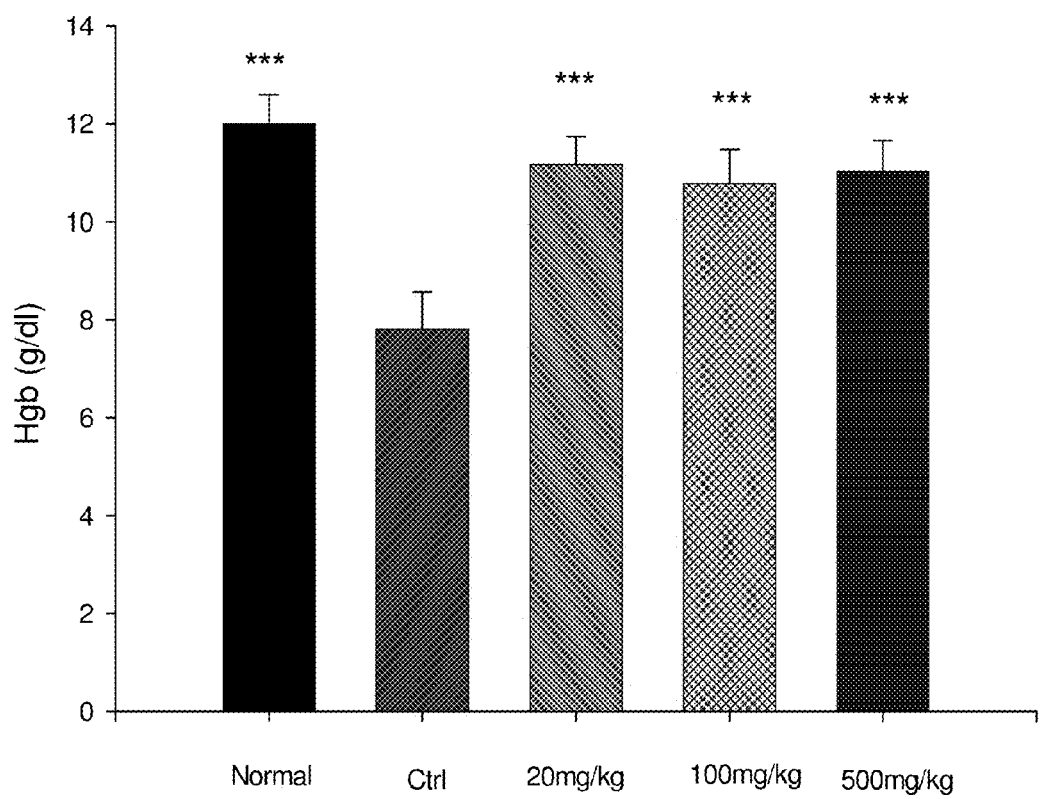
FIG. 10 is a bar graph showing the in vivo effect of the extract of *Dioscorea* sp. on hemoglobin content in the peripheral blood of cyclophosphamide (CP)-induced leukopenic mice suffering from severe anemia.

From the results shown in FIGS. 8-10, it is noted that the active extract of the present invention mitigates reduction of leukocyte number in peripheral blood and accelerates recovery of leukocytes, and maintains the red blood cells and Hbg content at normal levels.

Each and every patent, patent application and publication referred to herein is hereby incorporated by reference herein in its entirety.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for maintaining or enhancing the numbers of leukocytes and red blood cells in a chemotherapy patient, comprising orally administering to the patient an amount of a pharmaceutical composition, as a chemotherapeutic adjuvant, containing an effective amount of an extract of *Dioscorea* sp. for maintaining or enhancing the numbers of leukocytes and red blood cells in the patient to alleviate leukopenia side effects caused by the chemotherapy, wherein the extract of *Dioscorea* sp. is prepared by a process comprising (a) extracting a tuber of *Dioscorea alata* L. cv. Phyto with an alcohol-based solvent in the presence of 1% acetic acid to obtain a soluble fraction having the extract of *Dioscorea* sp., and the alcohol-based solvent is a methanol based solvent, an ethanol based solvent, or a mixture thereof.

2. The method according to claim 1, wherein the process to prepare the extract of *Dioscorea* sp. further comprises (b) extracting the soluble fraction with a solvent mixture of ethyl acetate and water so as to separate an ethyl acetate extract from a first water extracting existing in a firs water phase.

3. The method according to claim 2, wherein the process to prepare the extract of *Dioscorea* sp. further comprises (c) adding n-butanol solvent into the first water phase to perform further extraction so as to separate a butanol extract from a second water extract remaining in a second water phase.

4. The method according to claim 3, wherein the process to prepare the extract of *Dioscorea* sp. further comprises (d) adding 75% alcohol solvent into the second water phase to extract and further remove polysaccharide so as to obtain a purified water extract.

\* \* \* \* \*